United States Patent [19]
Johnson et al.

[11] Patent Number: 4,574,022
[45] Date of Patent: Mar. 4, 1986

[54] APPARATUS AND METHOD FOR TRANSFERRING AND APPLYING MATERIAL

[75] Inventors: Carl W. Johnson, Neenah; Stanley W. Kotschi, Oshkosh, both of Wis.

[73] Assignee: H. B. Fuller Company, St. Paul, Minn.

[21] Appl. No.: 586,137

[22] Filed: Mar. 5, 1984

[51] Int. Cl.⁴ .................................... B32B 31/08
[52] U.S. Cl. .................................. 156/164; 156/229; 156/474; 156/491; 156/121; 198/377
[58] Field of Search ............... 156/164, 229, 495, 494, 156/521, 542, 474, 205; 198/440, 441, 377

[56] References Cited

U.S. PATENT DOCUMENTS

| | | |
|---|---|---|
| 2,480,316 | 8/1949 | Blair et al. |
| 2,944,654 | 7/1960 | Schubert ........................ 198/377 |
| 3,026,231 | 3/1962 | Chavannes . |
| 3,215,250 | 11/1965 | Schubert ........................ 198/377 |
| 3,677,389 | 7/1972 | Benatar et al. ................ 198/377 |
| 3,728,191 | 4/1973 | Wiergba et al. ............... 156/556 X |
| 3,828,367 | 8/1974 | Bourgeois . |
| 3,854,861 | 12/1974 | Worrall . |
| 3,952,874 | 4/1976 | Owen ........................ 198/377 X |
| 3,960,641 | 6/1976 | Pedersen . |
| 3,963,557 | 6/1976 | Patterson . |
| 3,989,575 | 11/1976 | Davies ........................ 156/521 X |
| 4,022,456 | 5/1977 | Hooper et al. . |
| 4,081,301 | 3/1978 | Buell . |
| 4,227,952 | 10/1980 | Sabee . |
| 4,239,578 | 12/1980 | Gore . |
| 4,240,866 | 12/1980 | Rega . |
| 4,259,220 | 3/1981 | Bunnelle et al. . |
| 4,261,782 | 4/1981 | Teed . |
| 4,284,454 | 8/1981 | Joa . |
| 4,285,747 | 8/1981 | Rega ........................ 156/229 X |
| 4,293,367 | 10/1981 | Klasek et al. . |
| 4,297,157 | 10/1981 | Van Vliet . |
| 4,300,967 | 11/1981 | Sigl . |
| 4,309,236 | 1/1982 | Teed . |
| 4,333,782 | 6/1982 | Pieniak . |
| 4,353,762 | 10/1982 | Bouda . |
| 4,360,398 | 11/1982 | Sabee . |
| 4,364,787 | 12/1982 | Radzins . |
| 4,371,417 | 2/1983 | Frick et al. . |
| 4,379,016 | 4/1983 | Stemmler et al. ............ 156/164 X |
| 4,397,704 | 8/1983 | Frick . |
| 4,405,397 | 9/1983 | Teed . |
| 4,409,049 | 10/1983 | Passafiume . |
| 4,412,881 | 11/1983 | Sigl . |
| 4,413,623 | 11/1983 | Pieniak . |
| 4,417,935 | 11/1983 | Spencer . |
| 4,417,938 | 11/1983 | Sigl ........................... 156/164 X |
| 4,418,123 | 11/1983 | Bunnelle et al. ............. 156/164 X |

Primary Examiner—David Simmons
Attorney, Agent, or Firm—Merchant, Gould, Smith, Edell, Welter & Schmidt

[57] ABSTRACT

An apparatus and method for transferring and applying discrete lengths of material to a moving web is disclosed. The material is supplied to a plurality of applicator units (41). Each applicator unit (41) has a first applicator segment (42) and a second applicator segment (43). The applicator units (41) are rotated around a drum axis (35a). The web supply section (11) feeds the web (21) to a fluted corrugating roll (22). The first applicator segment (42) is rotated about a first axis and the second applicator segment (43) is rotated about a second axis, wherein the first and second applicator segments (42) and (43) are linearly aligned when passing under an extruder (27). Then the first and second applicator segments (42) and (43) rotate around the first and second axis to place the first and second applicator segments in space relationship when the material (33) is bonded to peaks (21a) of the web (21). Then the first and second applicator segments (42) and (43) rotate back around the first and second axis to place the first and second applicator segments back in linear alignment. The web removal section (15) removes the web (21) from the fluted corrugating roll (22) and pulls out the corrugations in the web (21), wherein the material (33) is stretched and bonded to the web (21) between the bonded peaks (21a).

36 Claims, 11 Drawing Figures

APPARATUS AND METHOD FOR TRANSFERRING AND APPLYING MATERIAL

BACKGROUND OF THE INVENTION

1. Field of the Invention

This invention relates generally to an apparatus and method for applying material, and more particularly to an apparatus and method for applying discrete lengths of a material to a moving web; such as, for example, applying a discrete length of elastic material to a disposable diaper bottom cover film.

2. Description of the Prior Art

Elastic material has been used in a variety of goods to provide an area that can be expanded or contracted to better fit the object on which the goods are placed. Examples of apparels on which elastic have been used are underwear, intimate wear, swimming wear, pants, skirts, jackets, fitted sheets, lab uniforms, diapers, and surgical garments, food related applications, such as porous holders/filters, i.e., for lemons. It also may be used to apply an elastic band around other articles, such as trash bags.

Typically, the elastic material has been secured to the goods by either stitching, heat sealing or an adhesive. Recently, the H. B. Fuller Company, Saint Paul, Minn., the assignee of the present application, developed a Fullastic TM material that is a pressure sensitive elastic that can replace sewn, heat-sealed or glued elastic in single use items such as disposable diapers, non-woven garments, surgical caps and drapes. The Fullastic TM material may also be used on reusable garments under certain circumstances, such as garments that can be washed in cold water. The Fullastic TM material is disclosed in U.S. Pat. No. 4,259,220 issued on Mar. 31, 1981 and U.S. Pat. No. 4,418,123 issued on Nov. 29, 1983. U.S. Pat. No. 4,259,220 discloses 2 methods of applying the pressure sensitive adhesive to a continuous substrate. The first method applies the pressure sensitive adhesive in a stretched state to a continuous substrate. The second method shows the pressure sensitive adhesive being applied in an unstretched state to a pregathered substrate. The Fullastic TM material can also be referred to as a self-adhering elastic, as well as a pressure sensitive adhesive.

One example of applying an elastic material to a diaper is disclosed U.S. Pat. No. 4,081,301 by Mr. Kenneth Buell. The patent discloses a method of applying a discrete, stretched, adhesively coated elastic material to predetermined portions of a disposable product at specified distances from the edge of the diaper. A method of applying discrete lengths of an elastic material, in an unstretched state, to a moving web is disclosed in U.S. Pat. No. 4,397,704 issued to Richard H. Frick. A continuous strip of adhesively coated material is severed into discrete lengths and transferred to a moving web. It is necessary to adhesively coat the elastic before applying it to the web material. In addition, if two separate, discrete lengths of material are to be applied in a space relationship to one another, it would be necessary for two sources of elastic material to be available. If the source of elastic material is an extruder, it would therefore be necessary to have two extruders available. This would increase the capital expenditures that are necessary to set up a manufacturing line.

U.S. Pat. No. 4,379,016 assigned to Winkler and Dunnebier discloses a method of spraying elastic strips onto a web of material used for making diapers. However, this patent provides for the spraying of the elastic material over the entire length of sections of the web. The elastic material is sprayed into the grooves of the web. Therefore, the elastic strip is adhered to the corrugated substrate in an unstretched state when the web is also gathered up. Further, an embossing roller having a tooth-like gear surface is used to form a multiplicity of fine folds in the web. Such a method and apparatus would again require two applicators to form two spaced part elastic members on a moving substrate.

The present invention addresses the problems associated with the prior art devices and provides for an apparatus and method for transferring a material, such as a self-adhering elastic extruded from a single source, and separating this extruded material into two distinct segments at a transfer point.

SUMMARY OF THE INVENTION

The present invention includes an apparatus and method of applying discrete lengths of an elastic material to a moving web. The apparatus includes a means for supplying an elastic material to a plurality of applicator units. Each applicator unit has a first applicator segment and a second applicator segment, wherein the material is supplied onto the first and second applicator segments. Means for rotating the plurality of applicator units around a drum axis is also provided. A means for feeding web to a means for creating web corrugations, having peaks and valleys in the moving web, are provided. Similarly, a means for bonding the material to the peaks of the moving web is provided. Means for rotating the first applicator segment around a first axis and the second applicator segment around the second axis is provided, wherein the first and second applicator segments are linearly aligned when passing under the supply means. Then, the first and second applicator segments rotate around the first and second axes to place the first and second applicator segments in spaced relationship when the material is bonded to the peaks of the web. Then, the first and second applicator segments rotate around the first and second axes to place the first and second applicator segments back in linear alignment. Also included in a means for removing the web from the web corrugating means and stretching out the web corrugations, wherein the material is stretched and bonded to the web between the bonded peaks.

The method of applying discrete lengths of elastic material to a moving web includes the steps of feeding a web material to a fluted corrugating roll, the fluted corrugating roll having an outer surface having a plurality of peaks and valleys and a plurality of holes. The web is caused to go into the valleys of the roll, thereby creating a corrugated web. The elastic material is transferred onto a plurality of applicator units. The plurality of applicator units are rotated around a drum axis, the first applicator segment is rotated around a first axis and the second applicator segment is rotated around a second axis, wherein the first and second applicator segments are linearly aligned when the elastic material is transferred to the applicator segments, then the first and second applicator segments rotate around the first and second axes to place the first and second applicator segments in spaced relationship. The elastic material is transferred from the applicator segments to the peaks of the moving web on the fluted roll. The rotation continues around the drum, first and second axes, wherein the first and second applicator segments rotate back to place the first and second applicator segments back in linear alignment. The web is removed from the fluted roll and the web is pulled to straighten the corrugated web out, wherein the material is stretched and bonded to the web between the peaks.

The invention also includes a method and apparatus for carrying and transferring materials. The apparatus includes a plurality of applicator units, each applicator unit having a first applicator segment and a second applicator segment, wherein the material to be transferred is placed on the first and second segments. A means for rotating the plurality of applicator units around a drum axis is provided. Also provided is a means for rotating the first applicator segment around a first axis and the second applicator segment around a second axis, wherein the first and second applicator segments are linearly aligned when the material is placed on the applicator segments, then the first and second applicator segments rotate around the first and second axes to place said first and second applicator segments in space relationship when the material is at a transfer point, then the first and second applicator segments rotate back around the first and second axes to place the first and second applicator segments back in linear alignment.

The method of carrying and transferring materials comprises placing the material to be transferred on a plurality of applicator units and rotating the plurality of applicator units around a drum axis. The first applicator segment is rotated around a first axis and the second applicator segment is rotated around a second axis, wherein the first and second applicator segments are linearly aligned when the material is transferred to the applicator units, then the first and second applicator segments rotate around the first and second axes to place the first and second applicator segments in space relationship. The material is transferred from the applicator segments when they are in a spaced relationship. The rotation around the drum, first and second axes is continued, wherein the first and second applicator segments rotate back to place the first and second applicator segments back in linear alignment.

BRIEF DESCRIPTION OF THE DRAWINGS

FIG. 11 is a second embodiment of an applicator unit for the present invention.

DETAILED DESCRIPTION OF THE PREFERRED EMBODIMENT

Figure 1:
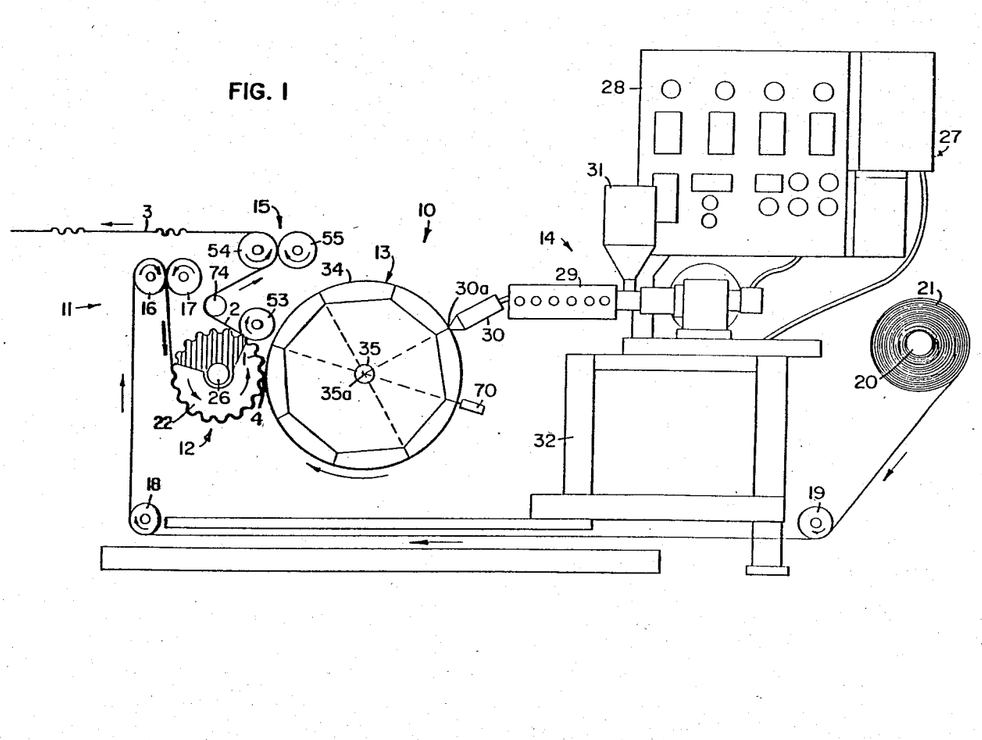
FIG. 1 is an schematic view of the apparatus incorporating my present invention.

Referring to the drawing, wherein like numerals represent like parts throughout the several views, there is generally disclosed at 10 an apparatus for applying elastic material to a moving web. The apparatus 10 includes a web supply section 11, web gathering section 12, material carrying and transfer section 13, material supply section 14, and a web removal section 15.

The web supply section 11 includes a pair of drive rolls 16 and 17 that drives the web of material 21 from the supply roll 20 around rolls 18 and 19 to the web gathering section 12. The web 21 may be any suitable roll of material, depending upon the nature of the product to be produced. For disposable diapers, the web 21 is typically a roll of polyethylene film. For garments, the web 21 is typically a non-woven material.

Figure 6:
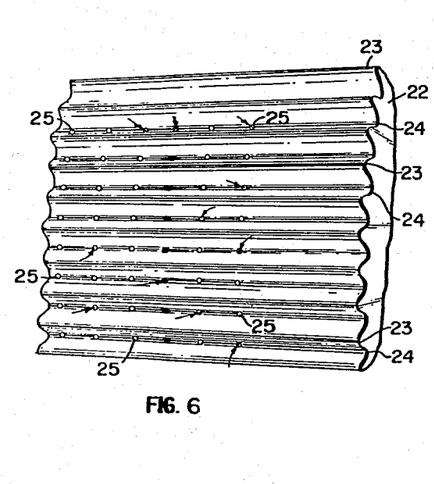
FIG. 6 is an perspective view of the corrugating drum of the apparatus shown in FIG. 1.

The web gathering section 12 includes a fluted corrugating roll 22 having an outer surface with a plurality of peaks 23 and valleys 24. A plurality of holes 25 are formed in the valleys 24 and are in communication with the interior of the roll 22. The roll 22 rotates on a shaft 26 that is driven by any suitable means well known in the art. In addition, the other rolls that are shown, such as rolls 16 and 17, are also provided with suitable drive means. It is also well known in the art how to rotate such rolls. A vacuum is created in the inside of the roll 22 by means well known in the art. The vacuum draws in air through the holes 25 and causes the web 21 that is supplied to the outer surface of the roll 22 to be drawn to go into the valleys 24. This therefore creates a gathered or creped web, having peaks 21a and valleys 21b corresponding to the peaks 23 and valleys 24 of the roll 22. It is understood that creping, fluting or web gathering are equivalent terms. In a preferred embodiment, a vacuum is only created in that section of the roll that is designated as 22a. There is no vacuum in the area that has been designated 22b. This likewise can be done by any method well known in the art. The vacuum is applied at the point where the web 21 first comes in contact with the roll 22 up until the point where the web 21 leaves the roll 22. By not having a vacuum in the area 22b, the web 21 is more easily taken from the roll 22, and the vacuum is conserved without leaks or uncovered vacuum holes.

It is understood for a porous web, it may be necessary to press the web into the valleys 24 of the corrugating roll 22 by appropriate means.

The material supply section 14 includes an extruder, generally designated as 27. The extruder 27 includes a control panel 28, extruder barrel 29, extruder nozzle 30, extruder feed section 31 and an extruder support table 32. The nozzle 30 may have a variable opening for extruding varying thickness of material. One example of a suitable extruder is model KLB-100 by Killion Extruders, Inc. of St. Verona, N.J. This extruder may be used for extruding a Fullastic TM material available from H. B. Fuller Company, Saint Paul, Minn., such as that sold and designated as their number HM-66-50. Further, an intermittant extruder, such as the Meltex "XP" extruder by Meltex Corporation of 404 Dividend Drive, Peachtree, Ga., or Nordson FlowMeter TM extruder by Nordson Corporation, 555 Jackson Street, Amherst, Ohio maybe used to extrude discrete segments of material 33.

Figures 2, 5:
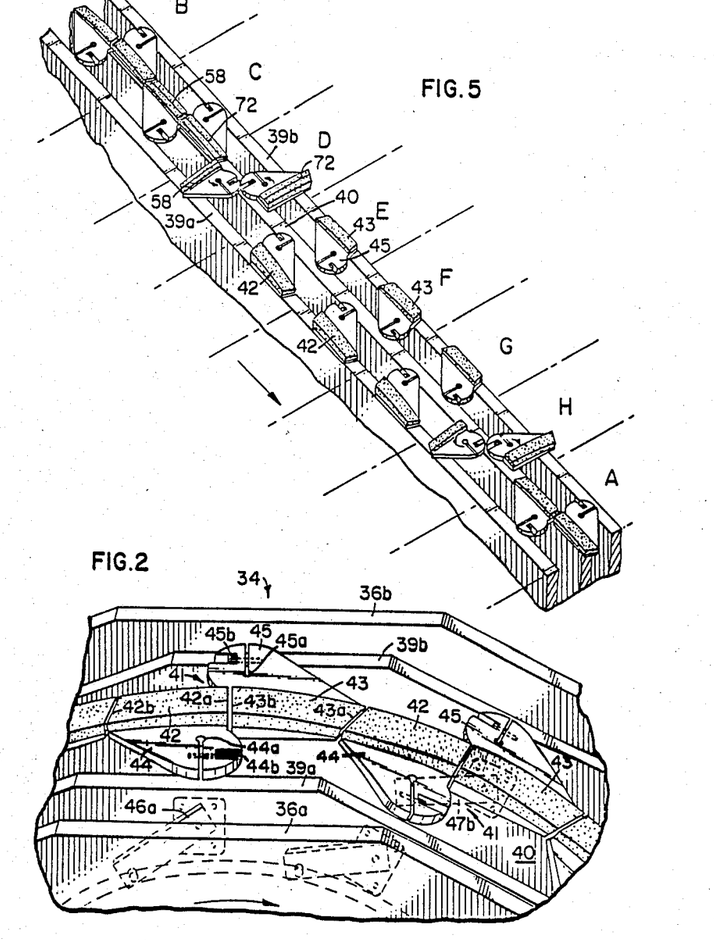
FIG. 2 is an enlarged perspective view of a portion of the transfer drum of the apparatus shown in FIG. 1.
FIG. 5 is an illustration of a portion of the transfer drum shown in a flat plane to illustrate the rotation of the individual applicator segments.
Figure 2:
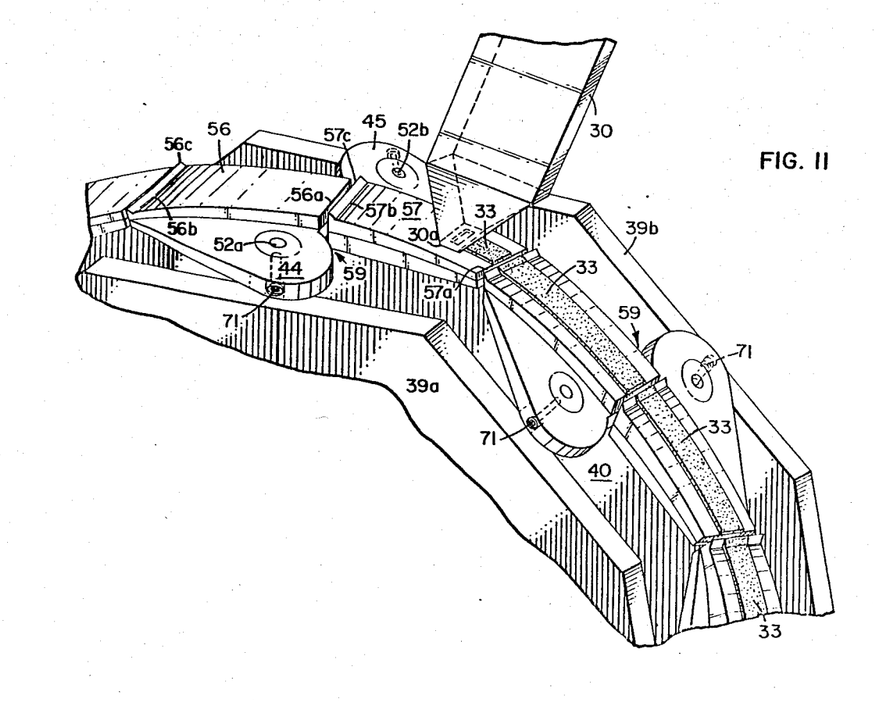

A continuous stream of self adhering elastic material 33 is extruded from the extruder nozzle 30, upon applicator segments 42 and 43 and adheres to these surfaces. The adhesive qualities of the self adhering material hold the material 33 to applicator segments 42 and 43 until they reach a transfer point 4, as will be more fully described hereafter. It is also understood that instead of using an extruder, it would be possible to use a roll of self adhering elastic material that has been previously formed into a continuous roll and coextruded with a backing. The continuous roll may then be used to as a supply to the carrying and transfer section 13. Further, it is also understood that instead of using a self adhering elastic, such as the Fullastic ™ material of H. B. Fuller, it would also be possible to use the present invention with a continuous roll of standard elastic material that is coated with an adhesive, on both surfaces or on one surface and by beld by vacuum on the applicator segments 42 and 43. Further, it is possible to use a material that has been precoated with adhesive that may be heat activated to make the coating adhesive. Still further, an elastic material that is coextruded with an adhesive may be used.

Applicant has found that if the tip 30a of the extruder nozzle 30 is held in close proximity to the applicator segments 42 and 43 there is good adhesion to the applicator segments.

Figure 3:
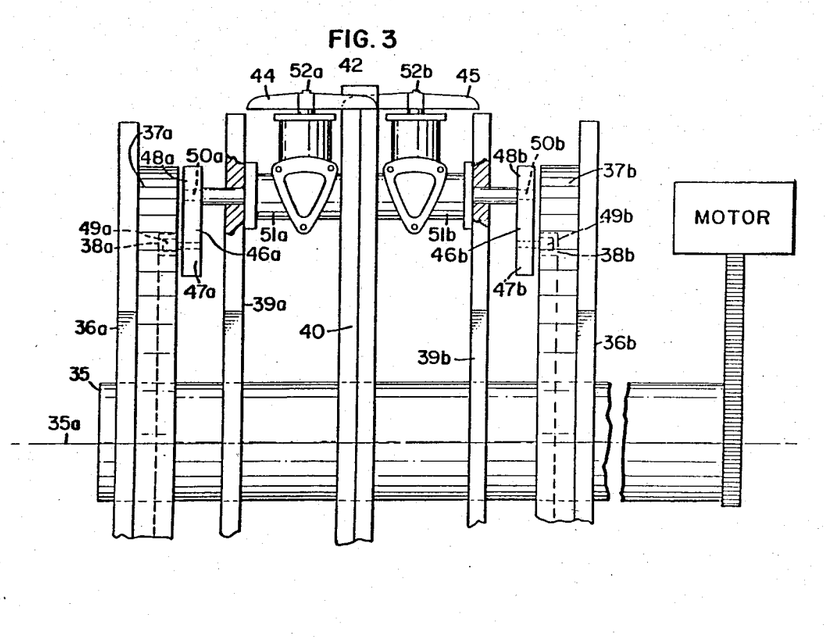
FIG. 3 is a front elevational view of the transfer drum of the apparatus as shown in FIG. 2. Also shown is the means for rotating a plurality of applicator units around a drum axis.

The carrying and transfer section 13 includes a transfer drum, generally designated as 34. The transfer drum 34 has a shaft 35 with an axis of rotation designated as 35a. Mounted on the shaft 35 by suitable bearing, not shown, for non-rotation about the axis 35a are cam wheel holders 36a and 36b, cams 37a and 37b. Gearbox support wheels 39a and 39b and applicator segment support wheel 40 are mounted on the shaft 35 for rotation about the axis 35a. One rotation of the shaft 35 for rotation about the axis 35a. One rotation of the shaft 35 also causes one rotation for the gear box support wheel 39a and 39b and applicator segment support wheel 40.

The carrying and transfer section 13 also includes a rotating knife wheel 70 that is used to cut the continuous band of elastic material 33 while it is held on the applicator segments 42 and 43. The knife wheel 70 will divide the band of material 33 into discrete segments, one segment held on applicator segment 42 and one segment held on applicator segment 43. Typically, the knife wheel 70 will be used with a non-extruded source of material. As will be more fully described hereafter, the knife wheel 70 may not be necessary with extruded material.

An alternate way of creating discrete segments is to an use an extruder which is capable of having a very fast on-off cycle such that discrete lengths of a pressure sensitive elastic material may be adhered to the applicator segments 42 and 43.

A plurality of applicator units, generally designated as 41, are cooperatively connected to the transfer drum 34, as will be more fully described hereafter. Each applicator unit comprises a pair of applicator segments, namely a first applicator segment 42 and a second applicator segment 43. The applicator unit 41 includes a first applicator segment 42 having a forward edge 42a and a trailing edge 42b and a second applicator segment 43 having a forward edge 43a and a trailing edge 43b. The forward edge 42a of the first applicator segment 42 and the trailing edge 43b of the second applicator segment 43 are generally at right angles to the sides of the respecting applicator segments. Since both the edge 42a and 43b both form a generally 90° angle with their sides, they can be positioned such that they are parallel with one another. Similarly, the forward edge 43a of the second applicator segment and the trailing edge 42b of the first applicator segment are both cut at an angle to form parallel surfaces. Cooperatively connected to the first applicator segment 42 is a supporting member 44. Similarly, cooperatively connected to the second applicator segment 43 is a supporting member 45. The first applicator segment 42 and second applicator segment 43 are supported over the applicator supporting wheel 40, but are free to rotate as will be more fully described hereafter. A first means for rotating the first applicator segment 42 and a second means for rotating the second applicator segment 43 are provided. However, only the first rotating means will be described in detail, as the second rotating means is similarly constructed.

Figure 4:
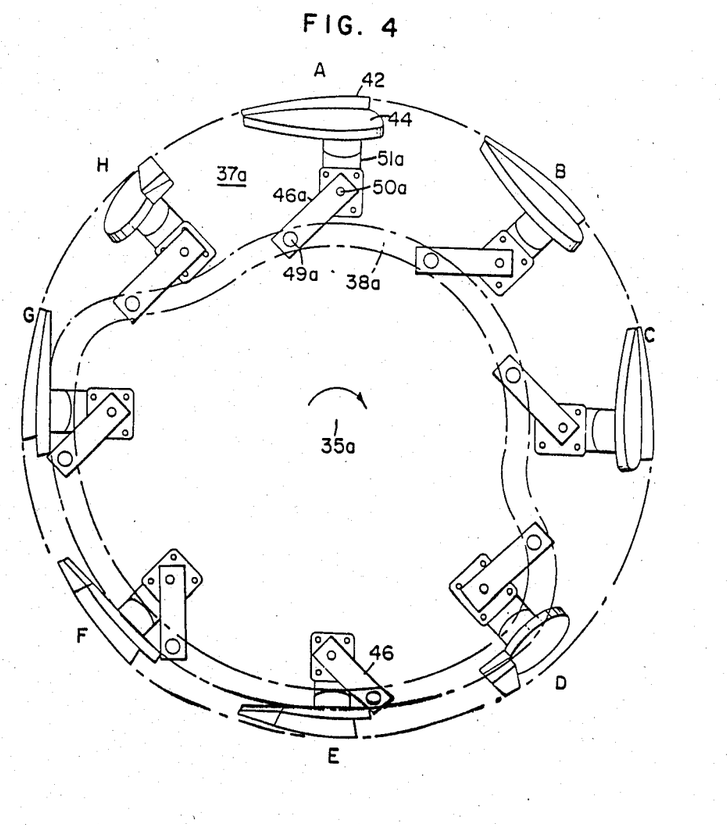
FIG. 4 is a side elevational view of the transfer drum as shown in FIG. 2 with portions removed to shown the movement along the cam track.

The means for rotating the first applicator segment 42 includes a cam track 38a configured in the cam 37a. A cam arm 46a having a first end 47a is in engagement with the cam track 38a. The engagement is by means of a roller 49a that is cooperatively connected to the first end 47a. The roller 49a rides in the cam track 37a. The second end 48a of the cam arm 46a is cooperatively connected to the input shaft 50a of a gearbox 51a. Any rotation of the cam arm 46a would therefore cause a like rotation of the input shaft 50a. The gearbox 51a is a right angle gear box having an input shaft 50a and an output shaft 52a. The rotation of the input shaft 50a is transmitted to the output shaft 52a by bevel gears (not shown). Further, there is step up ratio in the gearbox 51a such that one revolution of the input shaft 50a will cause two revolutions of the output shaft 52a. The gearbox 51a is suitably mounted in the gearbox support wheel 39a, by methods well known in the art. The gearbox 51a is also suitably mounted to the applicator support wheel 40. The input shaft 50a extends through the opening in the gearbox support wheel 39a in which the gearbox 51a is supported. The output shaft 52a is cooperatively connected to the support member 44, such that a rotation of the output shaft 52a causes the rotation of the support member 44 and the attached first applicator segment 42. One suitable method of cooperatively connecting the output shaft 52a to the support member 44 is to have an opening 44a in the support member 44 to which the output shaft 52a is secured by a set screw 44b. The applicator segment 42 rotates about an axis of rotation defined by the output shaft 52a. As shown in FIG. 4, there are eight pairs of applicator units 41 in the apparatus 10. Therefore, eight gearboxes 51a are secured at spaced intervals around the gearbox support wheel 39a.

As previously mentioned, a second rotating means provides for the rotation of the second applicator segment 43. The construction of the second rotating means is similar to that of the first rotating means. That is, a gearbox 51b having an input shaft 50b and output shaft 52b is supported in the gearbox support wheel 39b. A cam 37b is cooperatively connected to a cam wheel holder 36b and has configured therein a cam track 38b. A cam arm 46b having a first end 47b and second end 48b is provided. The first end 47b has cooperatively connected a roller 49b that rides in the cam track 38b. The second end 48b is cooperatively connected to the input shaft 50b. The output shaft 52b is cooperatively connected to the support member 45. One revolution of the input shaft 50b will cause two revolutions of the output shaft 52b. Also, the rotation of the output shaft 52b will cause rotation of the support member 45 and the attached second applicator segment 43.

The path of the cam track 38a is shown in FIG. 4. The path of the cam track 38b is a mirror image of that of the cam track 38a. The rotation of the first and second applicator segments 42 and 43 will be described more fully hereafter in the operation. Also, as will be more fully described hereafter, the elastic material 33 is transferred from the applicator segments 42 and 43 to the web 21 at a transfer point 4. The elastic material 33 is transferred to the peaks 21a of the web 21 and is bonded thereto.

To cool the material after it has been extruded onto the applicator segments and before it is transferred to the web 21 a fine mist of water may be sprayed on the material to cool it. Typically the material is extruded at a temperature of from 300° F. to 375° F. and should be cooled so that the web 21 will not melt. However, the temperature should stay above 90°. The temperature must be such that the material 21 is at a temperature that when it goes through rollers 54 and 55 (as will be described hereafter) the material will have adhesive qualities and still recover to its original length when not stretched.

The web removal section 15 includes a rubber coated roll 53 and a pair of pull rolls 54 and 55. The pull rolls 54 and 55 may be driven by any suitable means, well known in the art. Positioned between the pull rolls 54 and 55 and the roll 53 is a release coated idler roll 74. The idler roll 74 is not driven and is free to rotate at a fluctuating speed.

A second embodiment of the applicator unit is shown in FIG. 11. The second embodiment of the applicator unit is generally designated as 59. The applicator unit 55 includes a first applicator segment 56 having a forward edge 56a and a trailing edge 56b and a second applicator segment 57 having a forward edge 57a and a trailing edge 57b. The trailing edge 57b of the second applicator segment has a raised area 57c in the general shape of a triangle that extends along the entire back edge. Similarly, the trailing edge 56b of the first applicator segment has a raised area 56c, in the general shape of a triangle that extends along the back edge. The raised area 57c and 56c is typically 1/16 inch in height and ⅛ inch in length. The function of this raised edge is that similar to a wiper blade. That is, as the transfer drum 34 rotates, the raised area 56c and 57c will both come in close proximity to the tip 30a of extruder nozzle 30. This wiping action will temporarily interrupt the flow of elastic material 33 from the tip 30a of extruder nozzle 30. This slight interruption will cause the continuously extruded material to be adhered on the applicator segments 56 and 57 as discrete segments. Therefore, there will be no need to cut the extruded material into segments with a rotating knife wheel, as maybe necessary with the first embodiment of the applicator segments. A set screw 71 is used to connect the support members 44 and 45 to their respective shafts 52a and 52b.

Going back to the first embodiment of the applicator unit 41 with applicator segments 42 and 43 shown in FIG. 2, the extruded, continuous band of elastic adhesive 33 may be severed between each applicator segment 42 and 43 by rotating the applicator units 41 promptly after applying the elastic adhesive 30. The elastic adhesive 33 has low tear-strength properties at extruding temperature.

In operation, a roll of polyethylene film 21 is placed on roll 20. The film is fed around rolls 18 and 19 and through drive roll 16 and 17 to the corrugating drum 22. The corrugating drum 22 is rotating about its shaft and the film 21 is carried along the outer surface of the roll 22, with the film being sucked into the valleys 24 by means of a vacuum being applied through the holes 25. The film then rotates with the corrugated roll 22 and comes to a transfer point 4. At the transfer point 4, the counterrotating drum 34 and fluted corrugating roll 22 cause the web 21, at its peaks 21a to contact the elastic material 33 on the applicator segments 42 and 43 to be transferred, under the pressure between the drum 34 and roll 22 to the web 21. An elastic material, such as the previously discussed Fullastic TM material, is fed into the feeding section 31 of the extruder 27 and is extruded through the nozzle 30. The applicator segments 42 and 43 are in linear alignment as they pass under the extruder nozzle 30. The alignment is that of position A in FIGS. 5 and 6. The transfer drum 34 is rotating about its axis 35a. As the transfer drum 34 rotates, the cam arms 46a and 46b with rollers 49a and 49b are in their respective cam tracks 38a and 38b. The travel in cam track through positions B and C causes no rotation of the cam arms 46a and 46b. At this point, the knife wheel 70 may cut the elastic material 33 into discrete segments on the applicator segments 42 and 43. When the cam arms 46a and 46b travel through position D, the respective input shafts 50a and 50b are rotated 90°, causing the applicator segments 42 and 43 to rotate 180°. This places the applicator segments 42 and 43 in a spaced parallel relationship in position E. Position E is the transfer position and is the position of the applicator segments 42 and 43 at the transfer point 4. The elastic material 33 that has been extruded onto the applicator segments 42 and 43 is then bonded to the peaks 21a of the web 21 by a slight pressure. The applicator segments 42 and 43 are of a silicon rubber and the elastic 33 is transferred from the applicator segments 42 and 43 to the web 21. Alternately, the applicator segments 42 and 43 are of a polyurethane or a flurocarbon, such as Viton TM or Teflon TM by Dupont. At this point, the product being made would appear as in FIG. 8. Then, as the transfer drum continues to rotate, there is no rotation of the cam arms 46a and 46b through positions F and G. However, through position H, the cam arms are reverse rotated 90°, causing the applicator segments 42 and 43 to rotate 180°, bringing them back in linear alignment. In position D, the applicator segments 42 and 43 both rotate in a counterclockwise direction, and in position H, they rotate in a clockwise position.

In a preferred embodiment, the elastic material is extruded at position C. This allows for rotation in position D while the elastic material has a low tear strength and can be separated into segments simply by rotation of the applicator segments 42 and 43. Alternatively, the cam tracks 38a and 38b could be reconfigured such that the material could be extruded at position A and the rotation occur at position B instead of position D.

The material 33 is extruded along a longitudinal line 58 and 72 on the applicator segments 42 and 43. When viewed in FIG. 5, the lines 58 and 59 would lie along the same line, and are referred to as linearly aligned.

Figures 7, 9:
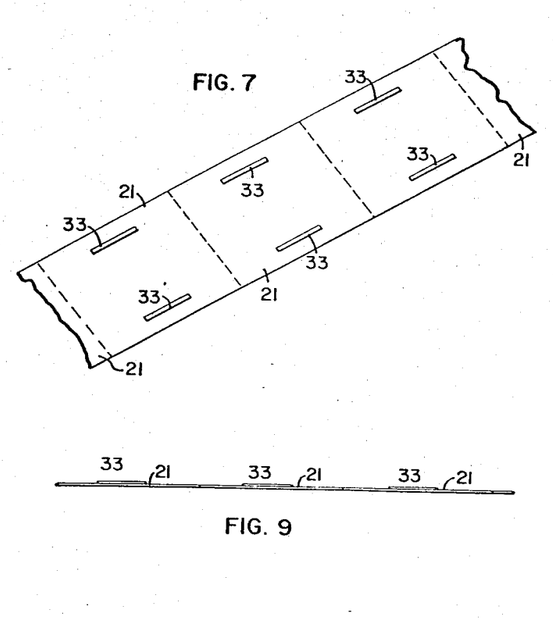
FIG. 7 is a perspective view of the product manufactured by the apparatus of FIG. 1.
FIG. 9 is a side elevational view of the product as it is being manufactured by the apparatus shown in FIG. 1 at position 2 in FIG. 1.
Figure 8:
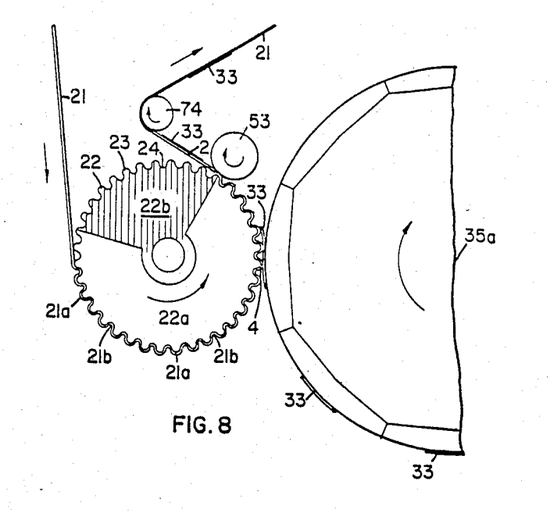
FIG. 8 is a side elevational view of the product as it is being manufactured by the apparatus shown in FIG. 1 at position 1 in FIG. 1.
Figure 10:
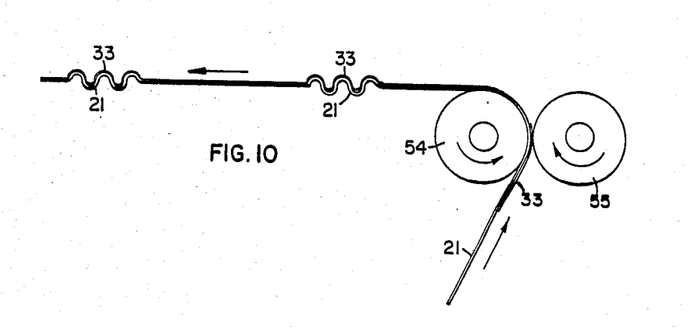
FIG. 10 is a side elevational view of the product as it is being manufactured by the apparatus shown in FIG. 1 at position 3 in FIG. 1.

In FIG. 8, there is illustrated the web 21 and elastic material 33 at the point designated as 1. That is, the elastic material 33 has been transferred to the web 21 and has been bonded to the peaks 21a. The pull rolls 54 and 55 are traveling at a faster speed than that of the fluted corrugating roll 22. Therefore, the corrugations in the corrugated web are pulled out. The idler roller 74 provides from removing the web 21 from the nip point between roller 22 and roller 53 tangentially. The web 21 is removed tangentially to prevent the material 33 from being wrapped around the roller 53. For the configuration shown, the speed of rollers 22 and 53 is one half that of rollers 16, 17, 54 and 55. As a valley 21b of the web 21 passes the nip point between the roller 22 and roller 53 it is necessary to accelerate the speed of the web 21. The idler roller 74 is free to rotate at varying speeds to provide for such acceleration. Alternately, the location of rollers 54 and 55 could be moved to provide for the tangential removal of the web 21 without the need for an idler roller 74. As these corrugations are pulled out in the position labeled 2 in FIG. 1, the adhesive material 33 is stretched and bonded to the web, while passing between the pull rolls 54 and 55 as shown in FIG. 9. Then, as the web moves past the pull rolls 54 and 55, and there is no longer a tension on the web, the elastic material 33 assumes its unstretched state, thereby gathering the web 21 along those areas where the elastic material has been applied. This is shown in FIG. 10. It is understood in actual production, other production steps may occur and it may be desirable to keep tension on the web 21. An example of a typical diaper construction is shown in FIG. 7. There, the elastic material 33 is 3 and ⅜ inches long in an unstretched state. In a stretched state, the adhesive would be 7 and ¼ inches long. A typical infant diaper is 14 and ½ inches in length. For an individual diaper, this leaves 3 and ⅝ inches on both sides of the adhesive strip. It is well understood in the art how to time the rotation of the roll 22 with that of the carrying and transfer section 13 to produce such a diaper configuration. The web 21, with the adhesive secured thereto, is then transferred to the next operation (not shown) of a diaper manufacturing operation.

The present invention provides for the transfer of material supplied in a continuous length or at one location to a second location and in discrete segments in a spaced relationship, thereby eliminating the need to have two sources of supply for the material.

It is understood that the material carrying and transfer section 13 may be used independently of the entire apparatus 10. That is, the carrying and transfer section 13 may be used to carry and transfer other articles that are supplied in a continuous strip that need to be transferred as separate discrete segments.

Other modifications of the invention will be apparent to those skilled in the art in light of the foregoing description. This description is intended to provide specific examples of individual embodiments which clearly disclose the present invention. Accordingly, the inventions are not limited to these embodiments or the use of elements having specific configurations and shapes as presented herein. All alternative modifications and variations of the present invention which follow in the spirit and broad scope of the appended claims are included.

What is claimed is:

1. An apparatus for applying discrete lengths of an elastic material to a moving web, said apparatus comprising:
   (a) means for supplying an elastic material;
   (b) a plurality of applicator units, each applicator unit having a first applicator segment and a second applicator segment, wherein said material is supplied onto said first and second applicator segments.
   (c) means for rotating said plurality of applicator segments around a drum axis;
   (d) means for creating corrugations, having peaks and valleys, in the moving web;
   (e) means for feeding the web to said corrugating creating means;
   (f) means for bonding said material to the said peaks of the moving web; and
   (g) means for rotating said first applicator segment around a first axis and said second applicator segment around a second axis, wherein said first and second applicator segments are linearly aligned when passing under said supply means, then said first and second applicator segments rotate around said first and second axes to place said first and second applicator segments in spaced relationship when said material is bonded to said peaks of the web, then said first and second applicator segments rotate around said first and second axes to place said first and second applicator segments back in linear alignment.

2. The apparatus of claim 1, further comprising a means for removing the web from said corrugation creating means and pulling out said corrugations, wherein said material is stretched and bonded to the web between the bonded peaks.

3. The apparatus of claim 1, wherein said supply means is an extruder, wherein said extruder extrudes said material onto said applicator segments.

4. The apparatus of claim 3, wherein said extruder extrudes an intermittent supply of material.

5. The apparatus of claim 3, wherein said material is extruded onto said first applicator segment along a first longitudinal line and onto said second applicator segment along a second longitudinal line, said first longitudinal line being in linear alignment with said second longitudinal line.

6. The apparatus of claim 3, wherein said first and second applicator segments are in spaced parallel relationship when said extruded material is bonded to said peaks of the web, wherein two discrete lengths of material are bonded in spaced parallel relationship to the web.

7. The apparatus of claim 1, wherein said applicator segments are made of silicon rubber.

8. The apparatus of claim 1, wherein said applicator segments are made of polyurethane.

9. The apparatus of claim 1, wherein said applicator segments are made of a flurocarbon.

10. The apparatus of claim 2, wherein said applicator segments each have a leading edge and trailing edge, and further comprising a means for interrupting the supply of said elastic material.

11. The apparatus of claim 10, wherein said interrupting means comprises a wiper.

12. The apparatus of claim 1, wherein said rotating means comprises a first rotating means for said first applicator segment and a second rotating means for a second applicator segment.

13. The apparatus of claim 12, wherein each of said rotating means comprises:
   (a) a cam track;
   (b) a cam arm having a first end in engagement with said cam track and a second end; and
   (c) a means for transferring a rotation of said cam arm to said applicator segment, said second end of said cam follower cooperatively connected to said transfer means.

14. The apparatus of claim 13, further comprising a supporting member cooperatively connected to each of said applicator segments.

15. The apparatus of claim 14, wherein said transfer means comprises a right angle gear box having an input shaft and an output shaft, said input shaft cooperatively connected to said second end of said cam arm and said output shaft cooperatively connected to said supporting member.

16. The apparatus of claim 15, wherein one revolution of said input shaft will turn said output shaft two revolutions.

17. The apparatus of claim 1, further comprising means for securing the material to the applicator segments.

18. The apparatus of claim 2, further comprising means for removing the web tangentially from said corrugation creating means.

19. An apparatus for applying discrete lengths of an elastic material to a moving web, said apparatus comprising:
 (a) an extruder for extruding an elastic material;
 (b) a plurality of applicator units, each applicator unit having a first applicator segment and a second applicator segment, wherein said material is extruded onto said first and second applicator segments, a supporting member cooperatively connected to each of said applicator segments;
 (c) means for securing the material to the applicator segments;
 (d) means for rotating said plurality of applicator units around a drum axis;
 (e) means for creating corrugations, having peaks and valleys, in the moving web;
 (f) means for bonding said material to the said peaks of the moving web;
 (g) a first rotating means for rotating said first applicator segment around a first axis and a second rotating means for rotating said second applicator segment around a second axis, each of said rotating means comprises:
  (i) a cam track;
  (ii) a cam arm having a first end in engagement with said cam track and a second end;
  (iii) a right angle gear box having an inputshaft and an output shaft, said input shaft cooperatively connected to said second end of said cam arm and said output shaft cooperatively connected to said supporting member, wherein said first and second applicator segments are linearly aligned when passing under said supply means, then said first and second applicator segments rotate around said first and second axes to place said first and second applicator segments in spaced relationship when said material is bonded to said peaks of the web, then said first and second applicator segments rotate back around said first and second axes to place said first and second applicator segments back in linear alignment; and
 (h) means for removing the web tangentially from said corrugating creating means and pulling out said corrugations, wherein said material is stretched and bonded to the web between the bonded peaks.

20. A material carrying and transfer apparatus for carrying and transferring an elastic material, comprising:
 (a) a plurality of applicator units, each applicator unit having a first applicator segment with a forward edge and a second applicator segment with a forward edge, wherein the elastic material to be transferred is placed on said first and second applicator segments said applicators units abutting each other as the material is applied;
 (b) means for rotating said plurality of applicator units around a drum axis; and
 (c) means for rotating said first applicator segment around a first axis and said second applicator segment around a second axis wherein said first and second applicator segments are linearly aligned when the material is placed on said applicator segments, then said first and second applicator segments rotate around said first and second axes to place said first and second applicator segments in sapced relationship and said forward edges aligned when the material is at a transfer point, then said first and second applicator segments rotate around said first and second axes to place said first and second applicator segments back in linear alignment wherein said applicator segments carry the material for at least a portion of the rotation around said drum axis.

21. The material carrying and transfer apparatus of claim 20, wherein said rotating means comprises a first rotating means for said first applicator segment and a second rotating means for a second applicator segment.

22. The material carrying and transfer apparatus of claim 21, wherein each of said rotating means comprises:
 (a) a cam track;
 (b) a cam arm having a first end in engagement with said cam track and a second end; and
 (c) a means for transferring a rotation of said cam arm to said applicator segment, said second end of said cam arm cooperatively connected to said transfer means.

23. The material carrying and transfer apparatus of claim 22, further comprising a supporting member cooperatively connected to each of said applicator segments.

24. The material carrying and transfer apparatus of claim 23, wherein said transfer means comprises a right angle gear box having an input shaft and an output shaft, said input shaft cooperatively connected to said second end of said cam arm and said output shaft cooperatively connected to said supporting member.

25. The material carrying and transfer apparatus of claim 23, wherein one revolution of said input shaft will turn said output shaft two revolutions.

26. A material carrying and transfer apparatus for carrying and transferring an elastic material, comprising:
 (a) plurality of applicator units, each applicator unit having a first applicator segment having a forward edge and a second applicator segment having a forward edge, wherein the elastic material to be transferred is placed on said first and second applicator segments, said applicator units abutting each other as the material is applied;
 (b) a supporting member cooperatively connected to each of said applicator segments;

(c) means for rotating said plurality of applicator units around a drum axis; and
(d) a first rotating means for rotating said first applicator segment around a first axis and a second rotating means for rotating said second applicator segment around a second axis, each of said rotating means comprises:
  (i) a cam track;
  (ii) a cam arm having a first end in engagement with said cam track and a second end;
  (iii) a right angle gear box having an input shaft and an output shaft, said input shaft cooperatively connected to said second end of said cam arm and said output shaft cooperatively connected to said supporting member, wherein said first and second applicator segments are linearly aligned when the material is placed on said applicator segments, then said first and second applicator segments rotate around said second and third axes to place said first and second applicator segments in spaced relationship and said forward edges aligned when the material is at a transfer point, then said first and second applicator segments rotate back around said first and second axes to place said first and second applicator segments back in linear alignment wherein said applicator segments carry the material for at least a portion of the rotation around said drum axis.

27. A method of applying discrete lengths of an elastic material to a moving web, said method comprising:
(a) feeding a web material to a corrugating roll, the corrugated roll, having an outer surface having plurality of peaks and valleys and a plurality of holes;
(b) causing the web to go into the valleys of the roll;
(c) transferring the elastic material onto a plurality of applicator units, each applicator unit having a first and second applicator segment, wherein the material is transferred onto said first and second applicator segments;
(d) holding the material on the applicator segments until the applicator segments reach a transfer point;
(e) rotating the plurality of applicator units around a drum axis;
(f) rotating the first applicator segment around a first axis and rotating the second applicator segment around a second axis, wherein said first and second applicator segments are linearly aligned when the elastic material is transferred to the applicator segments, then said first and second applicator segments rotate around the first and second axes to place the first and second applicator segments in spaced relationship;
(g) transferring the elastic material from the applicator segments to the peaks of the moving web on the corrugating roll;
(h) continuing the rotation around the drum, first and second axes, wherein the first and second applicator segments rotate to place the first and second applicator segments back in linear alignment; and
(i) removing the web from the corrugating roll and pulling the web straight, wherein the material is stretched and bonded to the web between the peaks.

28. The method of claim 27, wherein the elastic material is transferred to the applicator units by extruding the elastic material onto the applicator segments.

29. The method of claim 27, further comprising cutting the elastic material while on the applicator segments.

30. The method of claim 28, further comprising passing a wiper on the applicator segments in close proxmimity to the extruder to separate the elastic material into segments.

31. The method of claim 28, further comprising rotating the applicator segments while the extruded material is hot, whereby the extruded material is separated into discrete segments.

32. The method of claim 28, wherein the extruder intermittently extrudes the material.

33. The method of claim 27, wherein said web is removed tangentially.

34. A method of carrying and transferring elastic material, comprising:
(a) placing the material to be transferred onto a plurality of applicator units, each applicator unit having first and second applicator segments having forward edges, wherein the material is transferred onto the first and second applicator segments, said applicators units abutting each other as the material is applied;
(b) rotating the plurality of applicator units around a drum axis, wherein said applicator segments carry the material for at least a portion of the rotation around said drum axis;
(c) rotating the first applicator segment around a first axis and rotating the second applicator segment around a second axis, wherein said first and second applicator segments are linearly aligned when the material is transferred to the applicator units, then said first and second applicator segments rotate around the first and second axes to place the first and second applicator segments in spaced relationship;
(d) transferring the material from the applicator segments after being carried around at least a portion of the rotation around the drum axis when they are in a spaced relationship and the forward edges aligned; and
(e) continuing the rotation around the drum, first, and second axes, wherein the first and second applicator segments rotate to place the first and second applicator segments back in linear alignment.

35. The material carrying and transfer apparatus of claim 20, wherein the elastic material is supplied to the applicator units in a continuous form and wherein the continuous elastic material is separated into a first discrete component on said first applicator segment and a second discrete component on said second applicator segment when said first and second applicator segments rotate around said first and second axes.

36. The method of carrying and transferring an elastic material of claim 34, wherein the elastic material is supplied to the applicator units in a continous form and wherein when said first and second applicator segments rotate around the first and second axes the continous elastic material is separated into a first discrete component on said first applicator segment and a second discrete component on said second applicator segment.

* * * * *